US010317326B2

(12) United States Patent
Zuo et al.

(10) Patent No.: US 10,317,326 B2
(45) Date of Patent: Jun. 11, 2019

(54) TESTING DEVICE FOR INTEGRATED IRRIGATION AND DISINFECTION

(71) Applicant: Jiangsu University, Jiangsu (CN)

(72) Inventors: Zhiyu Zuo, Jiangsu (CN); Lijuan Qin, Jiangsu (CN); Hanping Mao, Jiangsu (CN); Xiaodong Zhang, Jiangsu (CN); Jiheng Ni, Jiangsu (CN); Qinglin Li, Jiangsu (CN); Tianyuan Lv, Jiangsu (CN)

(73) Assignee: Jiangsu University, Jiangsu (CN)

( * ) Notice: Subject to any disclaimer, the term of this patent is extended or adjusted under 35 U.S.C. 154(b) by 307 days.

(21) Appl. No.: 15/318,812

(22) PCT Filed: Dec. 9, 2015

(86) PCT No.: PCT/CN2015/096781
§ 371 (c)(1),
(2) Date: Dec. 14, 2016

(87) PCT Pub. No.: WO2016/176991
PCT Pub. Date: Nov. 10, 2016

(65) Prior Publication Data
US 2017/0115195 A1 Apr. 27, 2017

(30) Foreign Application Priority Data
May 6, 2015 (CN) .......................... 2015 1 0224500

(51) Int. Cl.
*G01N 11/02* (2006.01)
*A01G 25/16* (2006.01)
(Continued)

(52) U.S. Cl.
CPC ............ *G01N 11/02* (2013.01); *A01C 21/007* (2013.01); *A01C 23/008* (2013.01);
(Continued)

(58) Field of Classification Search
CPC ..... G01N 11/02; A01C 23/008; A01C 23/047; A01C 23/025; A01C 23/042; A01C 21/007; A01G 25/16; A01G 25/02; Y02A 40/237
(Continued)

(56) References Cited

U.S. PATENT DOCUMENTS

2013/0133260 A1* 5/2013 Solano Cabello ..... A01G 9/025
47/62 R

FOREIGN PATENT DOCUMENTS

CN 102163043 8/2011
CN 103141206 6/2013
(Continued)

*Primary Examiner* — Nathaniel T Woodward
(74) *Attorney, Agent, or Firm* — Miller Law Group, PLLC (57) ABSTRACT

A testing device for integrated irrigation and disinfection includes a centrifugal pump, pressure sensors, flow sensors, an ion concentration sensor, and a control system. The testing device has comprehensive functions of fertilization, spray and drip irrigation load simulation, water and fertilizer parameter detection, fertilizer absorbing channel parameter detection and backflow channel parameter detection. The detection of nutrient ion concentration in a nutrient solution is combined with the aspects of irrigation, dynamic preparation of a nutrient solution and disinfection of a nutrient solution, to realize a high-precision dynamic preparation of a nutrient solution and irrigation area load simulation, and satisfy the requirements on a test system during a research and development process of an irrigation and fertilization system. The testing device is applicable to the research on the techniques and the development of a system for precise irrigation and accurate preparation of a nutrient solution in the field of facility agriculture.

11 Claims, 4 Drawing Sheets

(51) Int. Cl.
*A01C 21/00* (2006.01)
*A01C 23/04* (2006.01)
*A01C 23/00* (2006.01)
*A01C 23/02* (2006.01)
*A01G 25/02* (2006.01)

(52) U.S. Cl.
CPC .......... *A01C 23/025* (2013.01); *A01C 23/042* (2013.01); *A01C 23/047* (2013.01); *A01G 25/16* (2013.01); *A01G 25/02* (2013.01); *Y02A 40/237* (2018.01)

(58) Field of Classification Search
USPC ...................................................... 73/118.01
See application file for complete search history.

(56) References Cited

FOREIGN PATENT DOCUMENTS

| | | |
|---|---|---|
| CN | 203040184 | 7/2013 |
| CN | 104798522 | 7/2015 |
| CN | 204634366 | 9/2015 |
| JP | 2000-23571 | 1/2000 |
| JP | 2015-80438 | 4/2015 |
| WO | 2014/200896 | 12/2014 |

\* cited by examiner

TESTING DEVICE FOR INTEGRATED IRRIGATION AND DISINFECTION

FIELD OF THE INVENTION

The present invention relates to an irrigating and disinfecting integrated testing device, which belongs to the precise irrigation field of modern agriculture and is mainly applicable for technology research and system development of facility agriculture precise irrigation and nutrient solution accurate preparation.

BACKGROUND OF THE INVENTION

In the aspects of irrigation, nutrient solution dynamic preparation, nutrient solution disinfection etc., at present, there are commercialized technical solutions and products all over the world; however, there are no corresponding technical solutions and products all over the word in the aspects of realization of high-precision nutrient solution dynamic preparation combined with the detection of nutrient iron concentration information of nutrient solution and satisfaction of the requirements of testing system during research and development process of fertilization system by simulation of irrigated area load.

An irrigating and disinfecting integrated testing device is the key supporting apparatus for the research of control technology and equipment in the facility agricultural environment, meanwhile, is also the fundamental testing apparatus for the research of the physiological information detection technology and mechanism of facility environment and crop, the growth and development and environment regulation model for the facility crop, control technology and equipment for the facility culturing environment.

The nutrient solution fertilization is one of key technologies in the facility agriculture, which comprising two parts: nutrient solution concentration preparation and irrigation. The preparation precision of nutrient solution concentration affects the nutrient supply of crops within the facility; the irrigation quantity and irrigation time affect the moisture supply of crops, and directly affect the quality and yield of crops, efficiency of agricultural facility and economic benefits of user. The research for the precision irrigation, precise fertilization and nutrient solution recovery and disinfection etc. has a significant meaning for improving the facility agricultural benefits and promoting the development of the facility agricultural industry.

SUMMARY OF THE INVENTION

The object of the present invention is to provide an irrigating and disinfecting integrated testing device, which has integrated functions of fertilization, residual liquid recovery and disinfection, spraying, dripping and irrigation load simulation, water and fertilizer parameter detection, fertilizer absorbing channel parameter detection and backflow channel parameter detection and the like, to realize the precise irrigation and nutrient solution precise preparation of the facility agriculture.

In order to solve the above technical problems, the present invention adopts the following technical solutions: an irrigating and disinfecting integrated testing device, wherein, comprising a fertilization pipeline, a residual liquid recovery and disinfection pipeline, a spraying, dripping and irrigation load simulation pipeline, a water and fertilizer parameter detection pipeline, a fertilizer absorbing channel parameter detection pipeline, a backflow channel parameter detection pipeline and a control system pipeline;

the fertilization pipeline comprising a water supply pump (2), a fertilization control electromagnetic valve (3), a fertilizer mixing tank (8), an irrigation pump (9), and an irrigation control electromagnetic valve (10) sequentially connected;

the spraying, dripping and irrigation load simulation pipeline comprising a proportion-control valve (16), controlling and measuring irrigation machines to be measured A (6) and controlling and measuring irrigation machines to be measured B (12), and pressure sensor A (22) and pressure sensor B (29) sequentially connected;

the water and fertilizer parameter detection pipeline comprising an irrigation machine to be measured (17), flow sensor A (21) and flow sensor B (30), pressure sensor A (22) and pressure sensor B (29), pH sensor A (15) and pH sensor B (27), EC sensor A (19) and EC sensor B (26), and a main nutrient element ion concentration transferring and transforming module (14) sequentially connected;

transfer switches are directly or indirectly connected in series in the control loops of each of the electromagnetic valve and pump drive motor; a "manual" branch in the transfer switch of an irrigated area control electromagnetic valve is further connected with a control switch in series, so that an electric control system can realize manual control, automatic control and complete switchover of irrigated area selection, water supply, fertilizer injection, nutrient solution preparation and irrigation/fertilization, so as to ensure that a zoning irrigation and a zoning variable fertilization can be carried out even if under a manual mode; the electric control system mainly comprises a variety of motor breaker protection devices, alternating current contactors, control relays, transfer switches, fuses, solid-state relays and control switches, which is mainly responsible for the control of the water supply pump (2), the irrigation pump (9), a fertilizer mixing control electromagnetic valve (4), a fertilization control electromagnetic valve (3), an irrigation control electromagnetic valve (10), an irrigated area control electromagnetic valve (13) and a fertilizer absorption control electromagnetic valve (28) and the switchover between the manual/automatic working mode;

an intelligent measuring and controlling system mainly comprises a microcontroller and peripheral interface circuits thereof, which is responsible for sending various control signals to the electric control system and detecting various operating status parameters in real time, such as a EC value of nutrient solution, pH value of a nutrient solution and an irrigation/fertilization flow, according to irrigation/fertilization modes and working parameters set by operators, to control the irrigation/fertilization process to be automatically performed in terms of set requirements.

The fertilization pipeline specifically works as follows: the water pump supplies water from a laboratory reservoir to the fertilizer mixing tank; the irrigation pump supplies water and fertilizer to the irrigated area; both of the water pump and the irrigation pump control the pressure and flow of the pipeline by means of frequency conversion and speed regulation.

The residual liquid recovery and disinfection pipeline works as follows: the residual liquids of the nutrient solution are collected from two culturing troughs and are temporarily stored in a liquid storage tank after filtered and disinfected, and at last, the residual liquids are added to the fertilizer mixing tank by a residual liquid adding device; disinfection is performed by means of ultraviolet ray plus ozone.

The spraying, dripping and irrigation load simulation pipeline works as follows: the water outlet pressures of the irrigation machines to be measured are controlled and measured by the proportion-control valve to realize the spraying, dripping and irrigation load simulation; the spraying, dripping and irrigation load simulation function realizes the performance detection for other fertilization systems and provides a basis for the performance detection of other fertilization systems.

The water and fertilizer parameter monitoring pipeline is used for measuring an water flow, a pressure, a pH value, an EC value and a main nutrient element ion concentration of the irrigation machine to be measured, so as to improve the precision and effectiveness for fertilization.

The fertilization absorbing channel parameter detection pipeline uses a weighing method to measure the flow of a mother solution.

The backflow channel parameter detection pipeline is used for measuring and controlling the pressure and flow of the fertilizer absorption backflow channel.

The main control system of the control system pipeline uses an industrial personal computer to collect and storage parameters, provides driving programs for a sensor and an execution mechanism, and opens a communication protocol and a control protocol; protection level is IP65.

The process of utilizing the above-mentioned testing device to realize the status monitoring for the fertilization step of an automatic fertilization machine is as follows: the status monitoring for the fertilization step in the fertilization working process of the automatic fertilization machine is realized depending on the flow meter A (21) and flow meter B (30); according to the current setting status for the irrigated area control, the current fertilization area and its size can be known, thereby estimating a theoretical fertilization flow. An actual fertilization flow is detected by the flow meter A (21) and flow meter B (30) and compared with the theoretical fertilization flow; if difference exceeds a predetermined limit, a failure must happen in the fertilization step, so an emergency treatment should be carried out immediately and an alarming prompt should be given; if the difference is within the predetermined limit, the fertilization step is considered as working normally.

The present invention has the following beneficial effects: on one hand, on the aspects of irrigation, nutrient solution dynamic preparation and the like, the detection of nutrient iron concentration information of nutrient solution is combined effectively to realize the high-precise nutrient solution dynamic preparation and irrigated area load simulation, so that more efficient fertilization is realized; on the other hand, the present invention can provide performance detection for other fertilization devices to satisfy the requirements on a testing system during a research and development process of a fertilization system.

In the drawings: 1. reservoir, 2. water supply pump, 3. fertilization control electromagnetic valve, 4. fertilizer mixing control electromagnetic valve, 5. liquid level control valve, 6. fertilization machine to be measured A, 7. sluice valve A, 8. fertilizer mixing tank, 9. irrigation pump, 10. irrigation control electromagnetic valve, 11. intelligent controller, 12. fertilization machine to be measured B, 13. irrigated area control electromagnetic valve, 14. ion concentration sensing and transforming module, 15. pH sensor A, 16. proportional valve, 17. irrigation machine, 18. filter, 19. EC sensor A, 20. sluice valve B, 21. flow sensor A, 22. pressure sensor A, 23. filter, 24. venturi, 25. electromagnetic valve, 26. EC sensor B, 27. pH sensor B, 28. fertilizer absorption control electromagnetic valve, 29. pressure sensor B, 30. flow sensor B, 31. rotor flow meter, 32. filter A, 33. filter B, 34. sluice valve C.

DETAILED DESCRIPTION OF THE PREFERRED EMBODIMENT

The specific implementation processes of the present invention are further illustrated below in conjunction with the accompanying drawings and specific embodiments.

The present invention mainly comprises a water supply pump 2, pressure sensor A22 and pressure sensor B29, flow sensor A21 and flow sensor B30, an ion concentration conversion module, a control system and the like, has functions of fertilization, residual liquid recovery and disinfection, spraying, dripping and irrigation load simulation, water and fertilizer parameter detection, fertilizer absorbing channel parameter detection, backflow channel parameter detection and the like. It is mainly applicable for the technology research and system development of facility agriculture precise irrigation and nutrient solution accurate preparation.

Figure 1A:
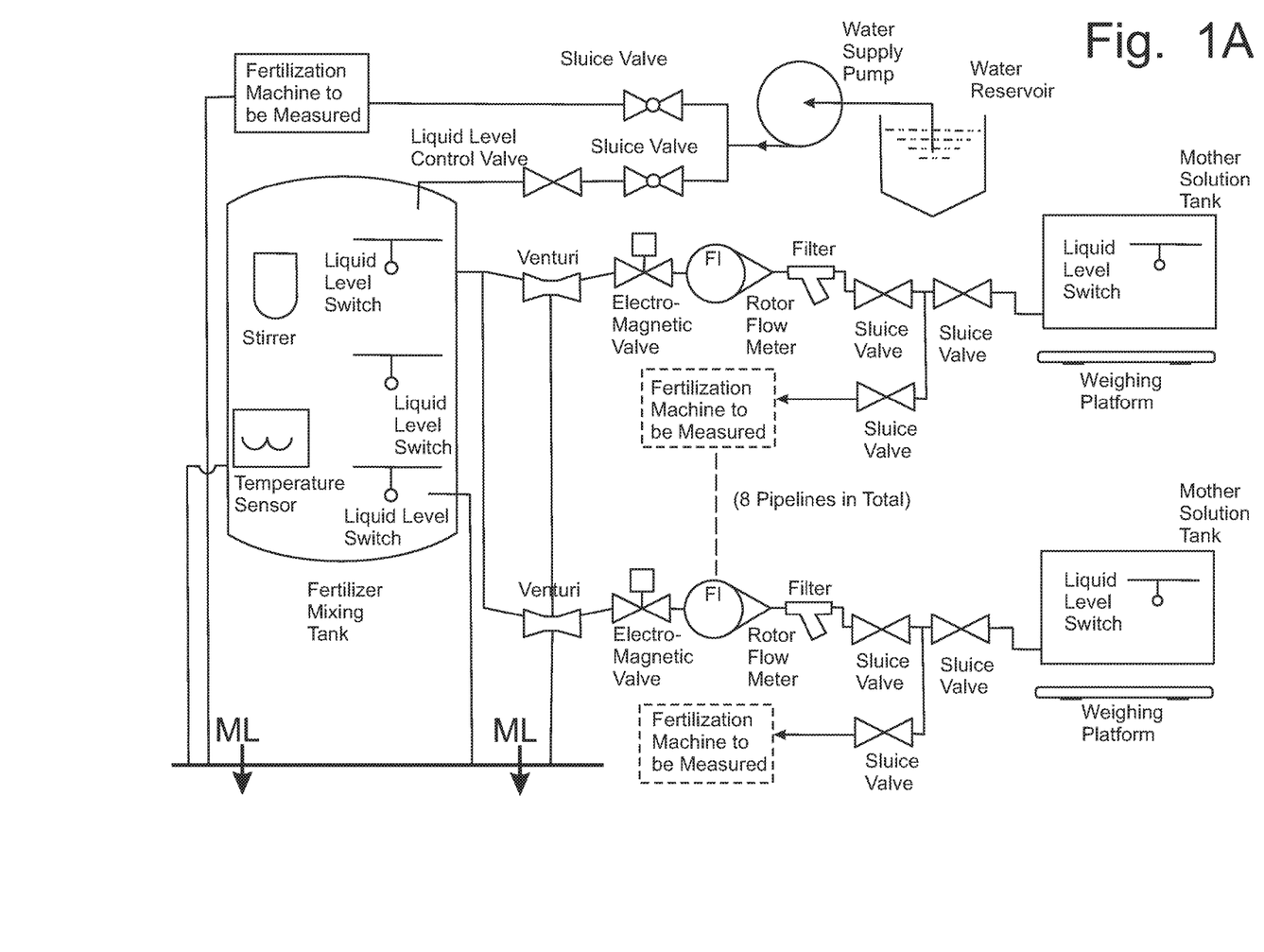
FIG. 1A is a portion of an overall structural schematic diagram of the present invention connected to FIG. 1B along the match line ML-ML.
Figure 1B:
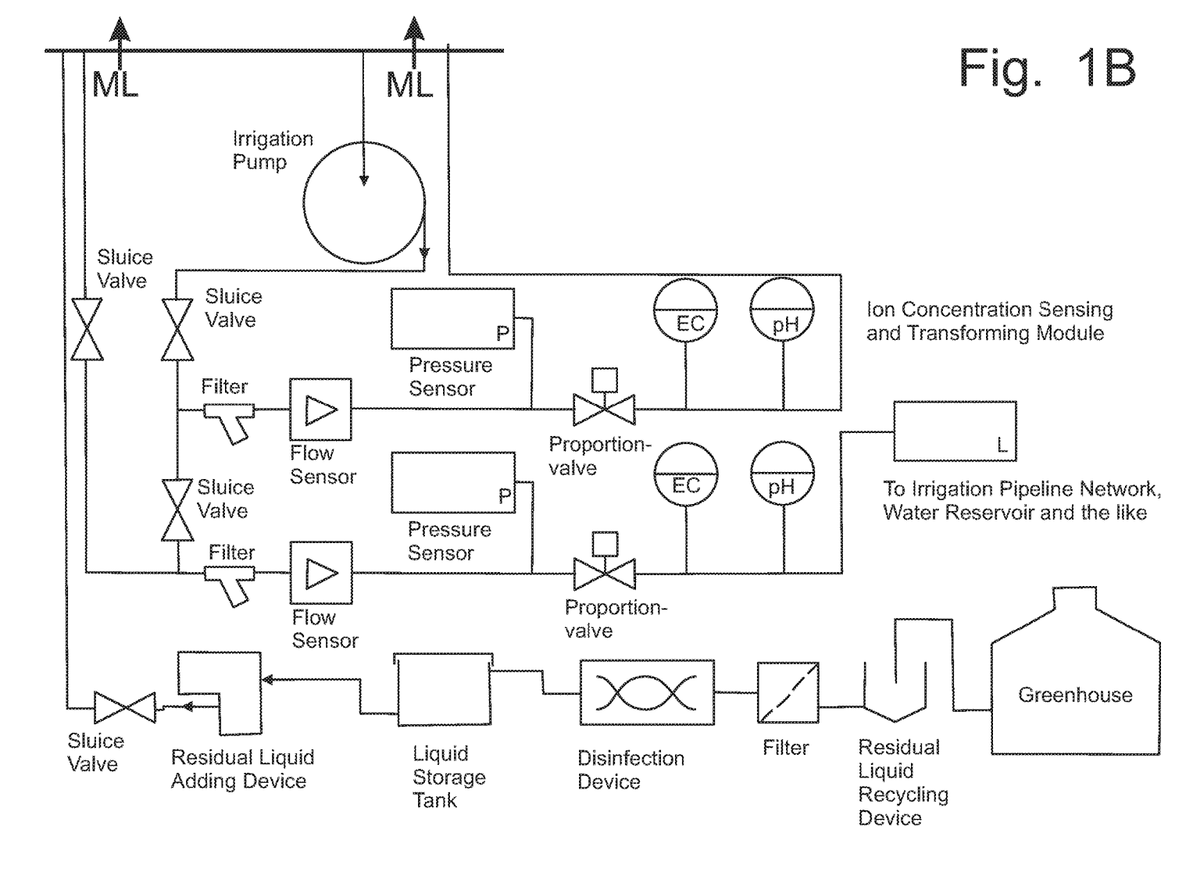
FIG. 1B is a second portion of the overall structural schematic diagram of the present invention connected to FIG. 1A along the match line ML-ML.
Figure 2:
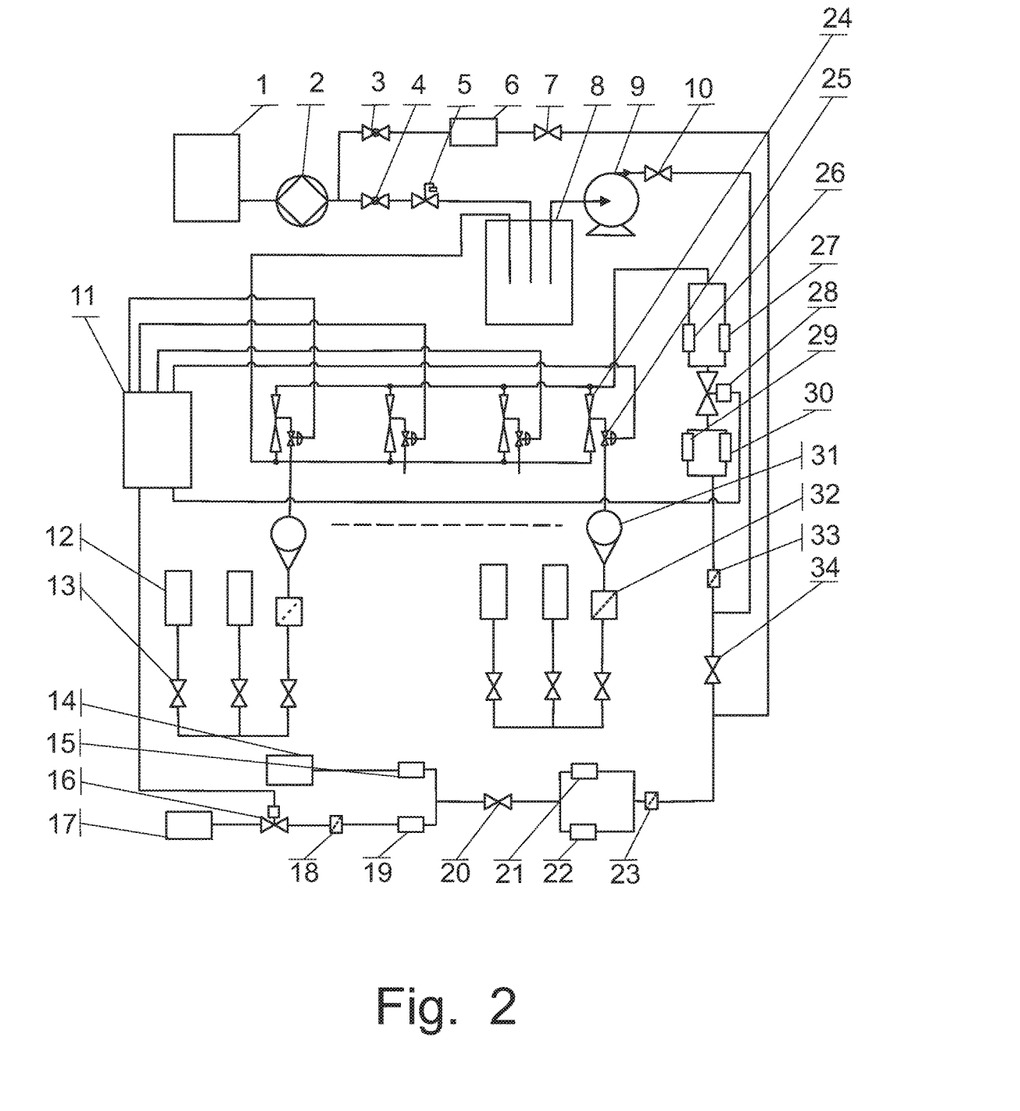
FIG. 2 is a system composition block diagram of the present invention.

The overall structural schematic diagram of the present invention is shown in FIG. 1, the present invention mainly comprises a centrifugal pump, pressure sensors, flow sensors, an ion concentration sensor, a control system and the like. A system composition block diagram is shown in FIG. 2.

The irrigating and disinfecting integrated testing device comprises a fertilization pipeline, a residual liquid recovery and disinfection pipeline, a spraying, dripping and irrigation load simulation pipeline, a water and fertilizer parameter detection pipeline, a fertilizer absorbing channel parameter detection pipeline, a backflow channel parameter detection pipeline and a control system pipeline. The fertilization pipeline comprises a water pump, a fertilization control electromagnetic valve, a fertilizer mixing tank, an irrigation pump, a sluice valve and the like sequentially connected; the spraying, dripping and irrigation load simulation pipeline comprises proportion-control valve 16, controlling and measuring irrigation machines to be measured A6 and irrigation machines to be measured B12, and pressure sensor A22 and pressure sensor B29; the water and fertilizer parameter detection pipeline comprises an irrigation machine to be measured 17, flow sensor A21 and flow sensor B30, pressure sensor A22 and pressure sensor B29, pH sensor A15 and pH sensor B27, EC sensor A19 and EC sensor B26, and main nutrient element ion concentration transferring and transforming module 14.

Figure 3:
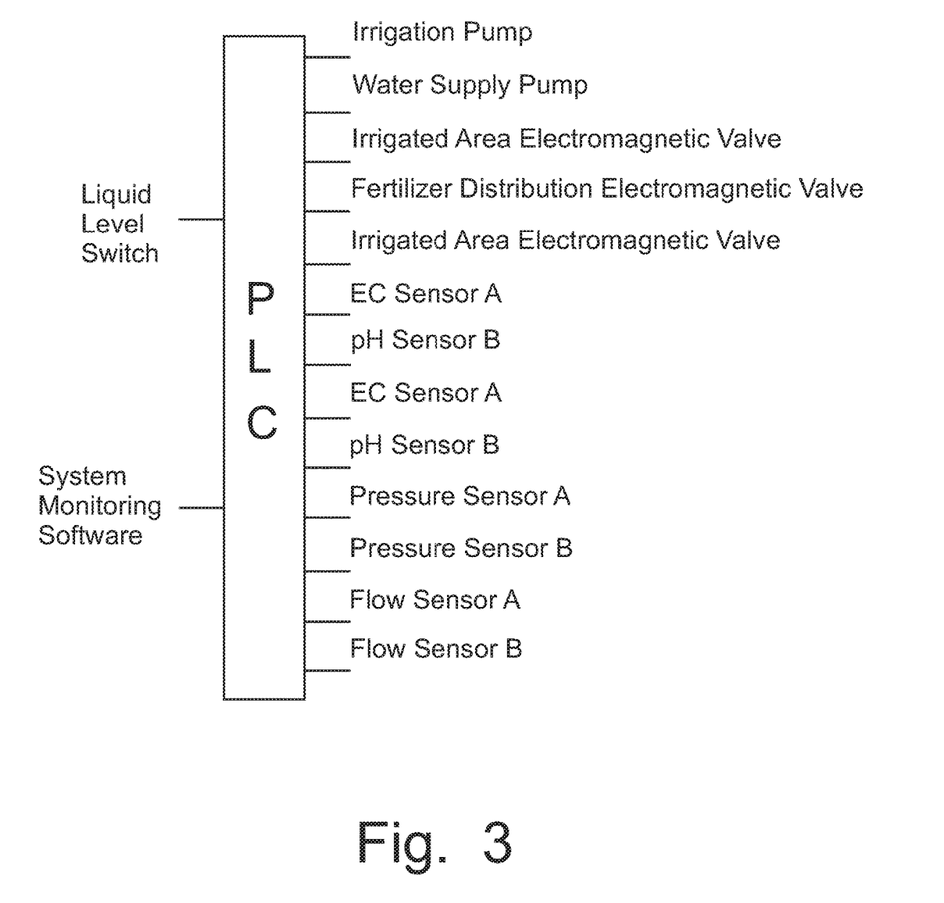
FIG. 3 is an electric control principle diagram of the present invention.

The electric control principle of the present invention is shown in FIG. 3. The electromagnetic valves and each pump are respectively connected to an electric control system that is connected with an intelligent measuring and controlling system; control mode transfer switches are respectively connected in series in the control loops of each of the electromagnetic valve and motor; each control mode transfer switch has manual and automatic branches; an irrigated control electromagnetic valve is connected with a solid-state relay; an irrigated area control mode transfer switch is connected in series in an input loop of the solid-state relay, an automatic position branch of the irrigated area control mode transfer switches is connected with an output signal end of the intelligent measuring and controlling system and a manual branch thereof is connected with an irrigated area control switch in series. An electromagnetic device control power, an input stage of the solid-state relay, an automatic branch of the control mode transfer switches and the intelligent measuring and controlling system are sequentially connected to form an automatic control loop of the solid-state relay; the control mode transfer switches connected in series in the control loop are irrigation control model transfer switch, fertilization control model transfer switch, fertilizer mixing control mode transfer switch and fertilizer absorbing control mode transfer switch, respectively.

The electromagnetic device control power, coils of fertilization pump on-off control relay which controls the fertilization pump and the manual branch of the fertilization pump control mode transfer switch are sequentially connected to form a manual control loop of the fertilization pump on-off control relay; the electromagnetic device control power, coils of the water supply pump on-off control relay, the automatic branch of the water supply pump control mode transfer switch and the intelligent measuring and controlling system are sequentially connected to form an automatic control loop of the water supply pump on-off control relay.

The main functions are as follows: the irrigating and disinfecting integrated testing device comprises a fertilization pipeline, a residual liquid recovery and disinfection pipeline, a spraying, dripping and irrigation load simulation pipeline, a water and fertilizer parameter detection pipeline, a fertilizer absorbing channel parameter detection pipeline, a backflow channel parameter detection pipeline and a control system pipeline; the fertilization pipeline comprises a water supply pump 2, a fertilization control electromagnetic valve 3, a fertilizer mixing tank 8, an irrigation pump 9, and an irrigation control electromagnetic valve 10 sequentially connected;

The status monitoring for the fertilization step during the fertilization operation of the automatic-fertilization machine is mainly realized by the flow meter A21 and flow meter B30. According to the current setting status for the irrigated area control, the current fertilization area and its size can be known, thereby estimating a theoretical fertilization flow. An actual fertilization flow is detected by the flow meter A21 and flow meter B30 and compared with the theoretical fertilization flow; if difference exceeds a predetermined limit, a failure must happen in the fertilization step, so an emergency treatment should be carried out immediately and an alarming prompt should be given; if the difference is within the predetermined limit, the fertilization step is considered as working normally.

The fertilization process of the present invention: the water pump supplies water from a laboratory reservoir to the fertilizer mixing tank; the irrigation pump supplies water and fertilizer to the irrigated area; both of the water pump and the irrigation pump control the pressure and flow of the pipelines by means of frequency conversion and speed regulation.

The residual recovery and disinfection part: the residual liquids of the nutrient solution are collected from culturing troughs (2 troughs) and are temporarily stored in a liquid storage tank after filtered and disinfected, and at last, the residual liquids are added to the fertilizer mixing tank by a residual liquid adding device. The disinfection of the present invention is performed by means of ultraviolet ray plus ozone.

The spraying, dripping and irrigation load simulation part: water outlet pressures of the irrigation machines to be measured are controlled and measured by the proportion-control valve to realize the spraying, dripping and irrigation load simulation. The spraying, dripping and irrigation load simulation function in the irrigating and disinfecting integrated testing device can realize the performance detection for other fertilization systems and provide a basis for the performance detection of other fertilization systems.

The water and fertilizer parameter detection part: measuring a water flow, a pressure, a pH value, an EC value and a main nutrient element ion concentration of the irrigation machine to be measured.

The fertilization absorbing channel parameter detection part: using a weighing method to measure the flow of a mother solution.

The backflow channel parameter detection part: measuring and controlling the pressure and flow of the fertilizer absorption backflow channel.

From the above, in the present invention, a transfer switch is directly or indirectly connected in series in the control loops of each of the electromagnetic valve and pump drive motor; a "manual" branch in the transfer switch of an irrigated area control electromagnetic valve is further connected with a control switch in series, so that an electric control system can realize manual control, automatic control and complete switchover of irrigated area selection, water supply, fertilizer injection, nutrient solution preparation and irrigation/fertilization, so as to ensure that a zoning irrigation and a zoning variable fertilization can be carried out even if under a manual mode. The electric control system mainly comprises a variety of motor breaker protection devices, alternating current contactors, control relays, transfer switches, fuses, solid-state relays and control switches, which is mainly responsible for the control of the water supply pump 2, the irrigation pump 9, a fertilizer mixing control electromagnetic valve 4, a fertilization control electromagnetic valve 3, an irrigation control electromagnetic valve 10, an irrigated area control electromagnetic valve 13 and a fertilizer absorption control electromagnetic valve 28 and the switchover between the manual/automatic operating mode; an intelligent measuring and controlling system mainly comprises a microcontroller and peripheral interface circuits thereof, which is responsible for sending various control signals to the electric control system and detecting various operating status parameters in real time, such as a nutrient solution EC value, a nutrient solution pH value and an irrigation/fertilization flow, according to irrigation/fertilization modes and operating parameters set by operators, to control the irrigation/fertilization process to be automatically performed in terms of set requirements.

In the above detailed description, a plurality of irrigated area control model transfer switches can be incorporated into one multi-section transfer switch; a plurality of fertilizer absorbing control mode transfer switches can also be incorporated into one multi-section transfer switch; the fertilization control model transfer switch and the irrigation control model transfer switch can be incorporated into one multi-section transfer switch, as well.

In the aspects of irrigation, nutrient solution dynamic preparation, nutrient solution disinfection etc., the technical solution of the present invention is effectively combined with the detection of nutrient solution nutrient iron concentration information to realize high-precision nutrient solution dynamic preparation and irrigated area load simulation, to satisfy the requirements on a testing system during a research and development process of a fertilization system.

Finally, it should be noted, the above embodiments are merely illustrative of the technical solution of the present invention rather than limiting. Although the present invention is illustrated in detail with reference to the preferred embodiments, it should be understood by those of ordinary skill in the art, modifications or equivalent replacements can be made to the technical solution of the present invention without departing from the spirit and scope of the technical solution of the present invention, which also fall within the scope of claims of the present invention.

The invention claimed is:

1. An irrigating and disinfecting integrated testing device, comprising:
 a fertilization pipeline to provide a flow of fertilizer laden water, a residual liquid recovery and disinfection pipeline connected to said fertilization pipeline to disinfect said flow of fertilizer laden water, a spraying, dripping and irrigation load simulation pipeline receiving said flow of fertilizer laden water from said residual liquid recovery and disinfection pipeline, a water and fertilizer parameter detection pipeline connected to said spraying, dripping and irrigation load simulation pipeline to measure fertilizer parameters within said flow of fertilizer laden water, said water and fertilizer parameter detection pipeline including a fertilizer absorbing channel parameter detection pipeline, a backflow channel parameter detection pipeline and a control system;
 the fertilization pipeline including a water supply pump, a fertilization control electromagnetic valve, a fertilizer mixing tank, an irrigation pump, and an irrigation control electromagnetic valve sequentially connected to said irrigation pump;
 the spraying, dripping and irrigation load simulation pipeline including a proportion-control valve, a first set of machines for controlling and measuring fertilization within irrigation to be measured and a second set of machines for controlling and measuring fertilization within irrigation to be measured, and a first pressure sensor;
 the water and fertilizer parameter detection pipeline including an irrigation machine to be measured, a flow sensor, a second pressure sensor, a pH sensor, an EC sensor, and a main nutrient element ion concentration transferring and transforming module sequentially connected to the pH sensor, the EC sensor and the irrigation machine to be measured; and
 the control system including transfer switches connected in series in control loops of each of the electromagnetic valves and a drive motor for said irrigation pump.

2. The irrigating and disinfecting integrated testing device of claim 1 further comprising:
 an electric control system including an irrigated area control electromagnetic valve provided with a transfer switch having a manual branch connected with a control switch in series, so that said electric control system can realize manual control, automatic control and complete switchover of irrigated area selection, water supply, fertilizer injection, nutrient solution preparation and irrigation/fertilization, so as to ensure that a zoning irrigation and a zoning variable fertilization can be carried out even if under a manual mode.

3. The irrigating and disinfecting integrated testing device of claim 2 wherein the electric control system comprises motor breaker protection devices, alternating current contactors, control relays, transfer switches, fuses, solid-state relays and control switches, which is responsible for the control of a water supply pump, an irrigation pump, a fertilizer mixing control electromagnetic valve, a fertilization control electromagnetic valve, an irrigation control electromagnetic valve, the irrigated area control electromagnetic valve and a fertilizer absorption control electromagnetic valve, along with the switchover between the manual and automatic operating modes.

4. The irrigating and disinfecting integrated testing device of claim 2 further comprising an intelligent measuring and controlling system including a microcontroller and peripheral interface circuits responsible for sending various control signals to the electric control system and detecting various operating status parameters in real time, including a nutrient solution EC value, a nutrient solution pH value and an irrigation/fertilization flow sensor, according to irrigation/fertilization modes and operating parameters selectively set by operators to control the irrigation/fertilization process to be automatically performed in terms of set requirements.

5. The irrigating and disinfecting integrated testing device of claim 1 wherein the water supply pump of the fertilization pipeline supplies water from a laboratory reservoir to a fertilizer mixing tank while the irrigation pump supplies water and fertilizer to the irrigated area, both the water pump and the irrigation pump control the pressure and flow of the pipelines by means of frequency conversion and speed regulation.

6. The irrigating and disinfecting integrated testing device of claim 1 wherein residual liquids of the nutrient solution within the residual liquid recovery and disinfection pipeline are collected from two culturing troughs and are temporarily stored in a liquid storage tank after being filtered and disinfected, the residual liquids being added to the fertilizer mixing tank by a residual liquid adding device, an ultraviolet ray plus ozone apparatus provides disinfection in the residual liquid recovery and disinfection pipeline.

7. The irrigating and disinfecting integrated testing device of claim 1 wherein water outlet pressures of the irrigation machines to be measured are controlled and measured by the proportion-control valve to realize the spraying, dripping and irrigation load simulation function within the spraying, dripping and irrigation load simulation pipeline, the spraying, dripping and irrigation load simulation function realizes the performance detection for other fertilization systems and provides a basis for the performance detection of other fertilization systems.

8. The irrigating and disinfecting integrated testing device of claim 1 wherein the water and fertilizer parameter detection pipeline is used for measuring water flow, pressure, pH value, EC value and main nutrient element ion concentration of the irrigation machine to be measured, so as to improve the precision and effectiveness for fertilization.

9. The irrigating and disinfecting integrated testing device of claim 1 wherein the fertilization absorbing channel parameter detection pipeline uses a weighing method to measure the flow of a mother solution.

10. The irrigating and disinfecting integrated testing device of claim 1 wherein the backflow channel parameter detection pipeline is used for measuring and controlling the pressure and flow of the fertilizer absorption backflow channel.

11. The irrigating and disinfecting integrated testing device of claim 1 wherein a main control system of the control system pipeline uses an industrial personal computer to collect and storage parameters, provides driving programs for a sensor and an execution mechanism, and opens a communication protocol and a control protocol with protection level at IP65.

\* \* \* \* \*